United States Patent [19]

Ohno et al.

[11] 4,012,428
[45] Mar. 15, 1977

[54] METHOD FOR PREPARING 3-METHYL-2-(4-HALOGENOPHENYL)-BUTYRONITRILE

[75] Inventors: Nobuo Ohno, Toyonaka; Takeaki Umemura, Takarazuka; Tetsuhiko Watanabe, Minoo, all of Japan

[73] Assignee: Sumitomo Chemical Company, Limited, Osaka, Japan

[22] Filed: Nov. 26, 1975

[21] Appl. No.: 635,548

[30] Foreign Application Priority Data

Nov. 26, 1974 Japan .............................. 49-136712

[52] U.S. Cl. ........................ 260/465 G; 260/465 F; 260/465 R
[51] Int. Cl.² ........................................ C07C 121/66
[58] Field of Search ..................... 260/465 R, 465 G

[56] References Cited

UNITED STATES PATENTS 3,413,309  11/1968  Makosza et al. ............... 260/465 X

OTHER PUBLICATIONS

Makosza et al.: Chemical Abstracts, vol. 64, pp. 12595–12596 (1966).
Lange: Chemical Abstracts, vol. 70, 37413h (1969).

*Primary Examiner*—Dolph H. Torrence
*Attorney, Agent, or Firm*—Sughrue, Rothwell, Mion, Zinn & Macpeak

[57] ABSTRACT

A method for preparing a 3-methyl-2-(4′-halogenophenyl)-butyronitrile which comprises alkylating a p-halogenophenylacetonitrile by reacting the p-halogenophenylacetonitrile with an isopropyl halide in the presence of an aqueous alkali metal hydroxide solution, using an organic guaternary ammonium salt as a catalyst.

4 Claims, 1 Drawing Figure

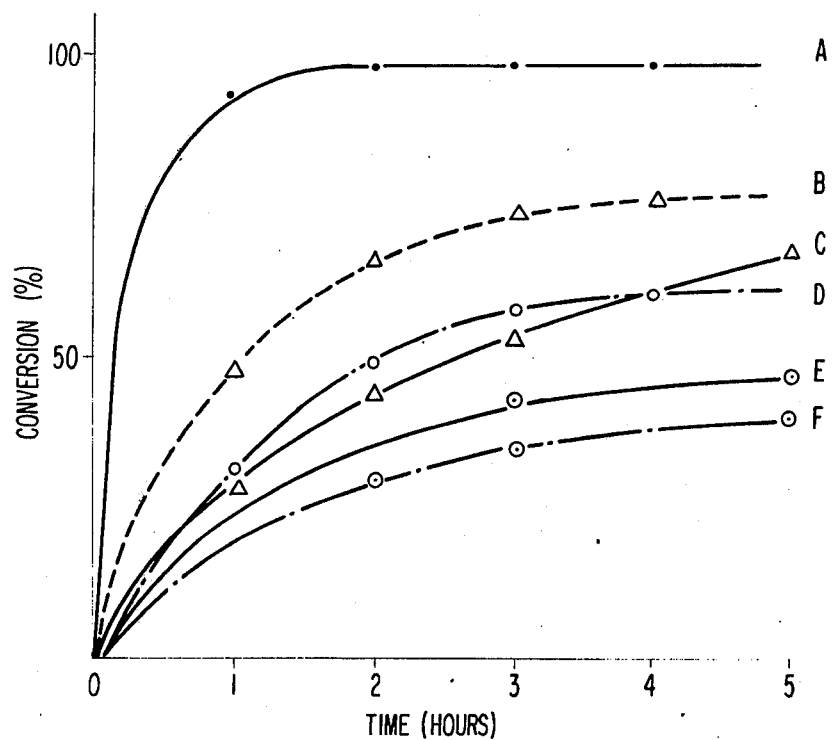

METHOD FOR PREPARING 3-METHYL-2-(4-HALOGENOPHENYL)-BUTYRONITRILE

BACKGROUND OF THE INVENTION

1. FIELD OF THE INVENTION

The present invention relates to a method for preparing a 3-methyl-2(4'-halogenophenyl)-butyronitrile.

2. DESCRIPTION OF THE PRIOR ART

In the conventional alkylation of phenylacetonitrile, phenylacetonitrile is reacted with an alkyl halide, in the presence of an alkali metal, alkali metal halide, alkali metal amide or the like as a base, in an anhydrous aprotic solvent or liquid ammonia. Details of the reaction conditions and yields are summarized in *Organic Reactions* Vol. 9, 297 (1957). However, many difficulties are encountered in handling large amounts of the above-mentioned bases so that this conventional method is not always advantageous for large scale industrial production. Furthermore, the yield and purity of the α-mono-alkylated phenylacetonitriles obtained are unsatisfactory.

Alkylation of the α-position, which has been recently developed, proceeds via the sodium salt of α-phenylacetoacetonitrile with an appropriate alcohol [*Journal of Organic Chemistry* Vol. 37, 526 (1972)]. This method gives relatively high yields when the alkyl groups introduced into the α-position are a straight chain alkyl group having more than 6 carbon atoms, but the yield is extremely low with lower or branched alkyl groups. Further, this method is not advantageous for industrial scale production since pressurized reaction vessels, such as an autoclave, are required in a case of lower alcohol. In recent years, a new alkylation process in which an organic quaternary ammonium salt is used as a phase transfer catalyst has been found, but for the reasons mentioned hereinafter this process is not completely acceptable.

A. Brändström et al. have reported [*Tetrahedron Letters* 473, (1972)] that when phenylacetonitrile is methylated with methyl iodide in methylene dichloride in the presence of a 7-10% aqueous sodium hydroxide solution using tetra-n-butyl-ammonium hydrogen sulfate (n-Bu$_4$N$^+$HSO$_4^-$) in an amount equimolar to the acetonitrile, the α-methylated product (72%), α, α-dimethylated product (14%), and the starting material (14%) are obtained as a mixture at a yield of 84%. When the alkylating agent is isopropyl iodide or ethyl iodide, the monoalkylated product alone is obtained at conversions of 75% and 90%, respectively, but 10 to 25% of the phenylacetonitrile used as the starting material remains unreacted. This method has two serious disadvantages: first, the alkyl iodide is expensive; second, on an industrial scale, such conversion levels make it necessary to separate the objective product from the resulting mixture, i.e., to use a separation procedure such as rectification. Furthermore, when the substituent at the α-position is a lower alkyl group, as desired by the inventors, even separation by a low cost technique such as rectification is not accessible.

M. Makosza et al. also studied the alkylation of phenylacetonitrile using quaternary ammonium salts as a catalyst, but satisfactory yields and purity could not be obtained. For example, they reported in *Roczniki Chem.* Vol. 39, 1223 (1965) and *Chemical Abstracts* Vol. 64, 12595 (1965) that when phenylacetonitrile is alkylated at room temperature with ethyl chloride in the presence of a 50% aqueous sodium hydroxide solution using benzyltriethyl ammonium chloride as a catalyst, 2-phenylbutyronitrile is obtained at a yield of 90%. The purity of the product was not disclosed, however.

For the alkylation of phenylacetonitrile where the benzene ring is substituted, it has been reported [*Roczniki Chem.* Vol. 42, 1619 (1968) and *Chemical Abstracts* Vol. 70, 37413 (1969)] that 4-bromophenylacetonitrile can be alkylated with α-chloroacetonitrile under the conditions used to obtain the α, α-di-cyanomethylated product at yields of 80%.

The inventors formerly investigated alkylation processes using organic quaternary ammonium salts as a catalyst, particularly for the isopropylation of a 4-halogenophenylacetonitrile, a important intermediate for an α-substituted phenylacetate (as disclosed in U.S. patent application Ser. No. 378,301, filed July 11, 1973), a novel new insecticide discovered by the inventors, which application is hereby incorporated by reference.

SUMMARY OF THE INVENTION

The inventors investigated the isopropylation of a 4-halogenophenylacetonitrile and found, surprisingly, that the 4-halogenophenylacetonitrile alone gives the α-isopropyl substitued product at exceptionally high conversions.

BRIEF DESCRIPTION OF THE DRAWING

The FIGURE shows conversion versus time for the isopropylation reaction, in which several kinds of substituted phenylacetonitriles are isopropylated with isopropyl bromide.

DETAILED DESCRIPTION OF THE INVENTION

In the reaction used to obtain the results for the Figure, a mixture of phenylacetonitrile (0.1 mole), isopropyl bromide (0.16 mole) and benzyltriethylammonium chloride (0.001 mole) in 40 ml of a 50% aqueous sodium hydroxide solution was stirred at 47° to 50° C. Sampling was carried out with the passage of time and the test samples were analyzed by gas chromatography. Then, the peak area ratio of the starting material to the α-isopropylated product was calculated on the gas chromatograph chart by the percentage method. The symbols A, B, C, D, E and F in the Figure indicate the following substituted phenylacetonitriles, respectively.

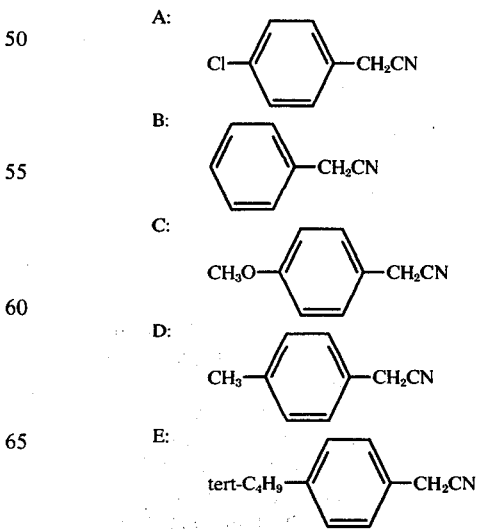

F:

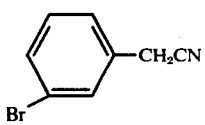
-continued

The 4-chloro analog (A) was alkylated quantitatively in two hours, while both the unsubstituted analog and the other substituted analogs gave only conversions of about 80% at the highest. Further, with the 4-chloro analog, the α, α-diisopropyl product was not produced at all, although isopropyl bromide was used in an amount as great as 1.6 times its equivalent weight.

In the reaction sought by the inventors, where a lower alkyl group was introduced into the α-position, the difference in the boiling point between the starting material and the objective product is so small that it is difficult to separate by rectification on an industrial scale. Therefore, a conversion level of about 80% is industrially insufficient.

The isopropylation reaction according to the present invention shows a characteristically rapid rate of reaction in the case of using the 4-halogenophenylacetonitrile alone, providing the objective α-mono-isopropylated product alone quntitatively. Thus, by the reaction of this invention it becomes possible for the first time to effectively isopropylate on an industrial scale.

The quaternary ammonium salts used as a catalyst can be freely selected, and examples of such salts are as follows:

Triethylbenzylammonium Chloride
Triethylbenzylammonium Bromide
Triethylbenzylammonium Iodide
Triethylbenzylammonium Hydroxide
Trimethylbenzylammonium Chloride
Trimethylbenzylammonium Bromide
Tetrabutylammonium Chloride
Tetrabutylammonium Bromide
3-Phenoxybenzyltriethylammonium Bromide
Tripropylbenzylammonium Chloride
Triethylpropylammonium Bromide
Cetyltriethylammonium Bromide
m-Octyltrimethylammonium Chloride
p-Methoxybenzyltriethylammonium Chloride The amount of the catalyst used can be optionally selected within the range of 1/200 to 1/5 mole per mole of the phenylacetonitrile, but about 1/100 mole of catalyst per mole of the phenylacetonitrile is sufficient for practical purposes.

The concentration of the aqueous alkali metal hydroxide solution, for example, an aqueous sodium hydroxide or potassium hydroxide solution, may be optionally selected within the range of 10 to 70%. Use of dilute solutions tends to reduce the rate of reaction slightly. From the practical viewpoint, a concentration of from 40% to 60%, more preferably about 50%, is used.

The concentration of the aqueous alkali metal hydroxide solution in the reaction system generally ranges from about 1 to 15, preferably 1 to 7, most preferably 2 to 4, times the weight of the reactants.

The reaction temperature can be optionally selected within the range of room temperature to 120° C, but temperatures in the vicinity of room temperature reduce the rate of reaction. The temperature is preferably from 40° to 70° C, most preferably from 45° to 60° C.

The rate of reaction varies depending upon the isopropyl halide used, but both the chloride and bromide can be used; in general, however, the bromide provides a superior rate of reaction. The isopropyl halide used can be used in any molar amount greater than 1.0 mole of the isopropyl halide per mole of phenylacetonitrile. From a practical viewpoint, 1.1 to 1.5 moles of the isopropyl halide per mole of phenylacetonitrile is preferred.

The pressure employed in the reaction is generally atmospheric pressure.

The use of a solvent, for example, benzene, toluene, chloroform, 1,2-dichloroethane, methylenedichloride, etc., is not necessary, but if used, it does not retard the reaction.

The present invention will be illustrated in more detail with reference to the following examples; however the present invention is not limited to these examples.

EXAMPLE 1

22.7 g (0.15 mole) of p-chlorophenylacetonitrile, 22.14 g (0.18 mole) of isopropyl bromide and 0.342 g (0.0015 mole) of triethylbenzylammonium chloride were charged into a reaction vessel, and 60 ml of a 50% aqueous sodium hydroxide solution added dropwise to the resulting mixture over 1 hour while water-cooling. After the dropwise addition was completed, the mixture was gradually heated to 55° C and stirred for 6 hours at 55° C. Thereafter, the reaction mixture was allowed to cool to room temperature, and it was diluted with 50 ml of water and 100 ml of benzene while stirring, whereafter the benzene layer was separated. The remaining aqueous layer was extracted with 100 ml of fresh benzene and all benzene layers obtained were combined and washed with a saturated aqueous sodium chloride solution. The benzene was removed under reduced pressure and the residue obtained subjected to vacuum distillation to obtain 26.5 g of a distillate having a boiling point of 100°–112° C/0.8 mmHg. The yield was 91.4%.

3-Methyl-2-(4'-chlorophenyl)-butyronitrile thus obtained was analyzed by gas chromatography, and less than 0.2% p-chlorophenylacetonitrile (starting material) and less than 1.0% 3-methyl-2-isopropyl-2-(4'-chlorophenyl)-butyronitrile (α, α-diisopropylated product) were detected as impurities (the values were obtained by the percentage method).

EXAMPLE 2

A reaction was carried out in the same manner as described in Example 1 except for using 0.483 g (0.0015 mole) of tetrabutylammonium bromide as the catalyst instead of triethylbenzylammonium chloride.

It took 9 hours to complete the reaction. The amount of product obtained was 25.8 g (yield: 89%). Results of gas chromatographic analysis were the same as obtained in Example 1.

EXAMPLE 3

A reaction was carried out in the same manner as described in Example 1 except for using 0.546 g (0.0015 mole) of 3-phenoxybenzyltriethylammonium bromide as the catalyst instead of triethylbenzylammonium chloride.

It took 8 hours to complete the reaction. The amount of product obtained was 26.4 g (yield: 90.9%). Results of gas chromatographic analysis were the same as obtained in Example 1.

EXAMPLE 4

A reaction was carried out in the same manner as described in Example 1 except that 60 ml of a 40% aqueous sodium hydroxide solution was used in place of the 50% aqueous sodium hydroxide solution. The amount of product obtained was 25.6 g (yield: 88.1%). Gas chromatographic analysis showed that 1% of the starting material and less than 1% of the dialkylated product were present as impurities.

EXAMPLE 5

A reaction was carried out in the same manner as described in Example 1 except that the reaction temperature was 70° C. Five hours were required for completion of the reaction. The amount of product obtained was 25.7 g (yield: 88.5%). Gas chromatographic analysis established 3% phenylacetonitrile (starting material) was present as the main impurity.

While the invention has been described in detail and with reference to the specific embodiments thereof, it will be apparent to one skilled in the art that various changes and modifications can be made therein without departing from the spirit and scope thereof.

What is claimed is:

1. A method for preparing a 3-methyl-2-(4'halogenophenyl)-butyronitrile which comprises isopropylating, at a temperature between room temperature and 120° C, a p-halogenophenylacetonitrile with an isopropyl halide in the presence of an organic quaternary ammonium salt selected from the group consisting of triethylbenzylammonium chloride, triethylbenzylammonium bromide, triethylbenzylammonium iodide, triethylbenzylammonium hydroxide, trimethylbenzylammonium chloride, trimethylbenzylammonium bromide, tetrabutylammonium chloride, tetrabutylammonium bromide, 3-phenoxybenzyl-triethylammonium bromide, tripropylbenzylammonium chloride, triethylpropylammonium bromide, cetyltriethylammonium bromide, m-octyltrimethylammonium chloride, and p-methoxybenzyltriethylammonium chloride, as a catalyst, and in the presence of an aqueous alkali metal hydroxide solution, wherein said ammonium salt catalyst is present in an amount of from 1/200 to 1/5 mole per mole of the phenylacetonitrile, and wherein the concentration of said alkali metal hydroxide solution is 10 to 70% by weight.

2. The method according to claim 1, wherein the concentration of the alkali metal hydroxide solution is 40% to 60%, by weight.

3. The method according to claim 1, wherein the reaction is carried out at a temperature ranging from 45° to 60° C.

4. The method according to claim 1 wherein the amount of said aqueous metal hydroxide solution in the reaction system ranges from about 1 to 15 times the weight of the reactants.

* * * * *